United States Patent [19]
Chudnovsky

[11] Patent Number: 6,157,033
[45] Date of Patent: Dec. 5, 2000

[54] LEAK DETECTION SYSTEM

[75] Inventor: Bella Helmer Chudnovsky, Mason, Ohio

[73] Assignee: Power Distribution Services, Inc., Westchester, Ohio

[21] Appl. No.: 09/080,415

[22] Filed: May 18, 1998

[51] Int. Cl.[7] .................................................. G01N 21/35
[52] U.S. Cl. ................... 250/338.5; 250/339.06; 250/339.11; 250/339.13; 250/341.1
[58] Field of Search ........................... 250/338.5, 339.06, 250/339.11, 339.12, 339.13, 347, 341.8; 356/51

[56] References Cited

U.S. PATENT DOCUMENTS

| 3,976,884 | 8/1976 | Acton . | |
|---|---|---|---|
| 4,390,785 | 6/1983 | Faulhaber et al. | 250/330 |
| 4,489,239 | 12/1984 | Grant et al. | 250/339 |
| 4,543,481 | 9/1985 | Zwick . | |
| 4,555,627 | 11/1985 | McRae . | |
| 4,996,431 | 2/1991 | Bonne et al. | 250/343 |
| 5,161,408 | 11/1992 | McRae et al. | 73/40.7 |
| 5,430,293 | 7/1995 | Sato et al. | 250/330 |
| 5,656,813 | 8/1997 | Moore et al. | 250/330 |

OTHER PUBLICATIONS

H.S. Lee, H.H. Zwick. Gas Filter Correlation Instrument for the remote sensing of gas leaks. Rev. Sci. Instrum, Sep. 1985, p. 1812–1819, v56, N9, USA.

Thomas G. McRae and Thomas J. Culp. Backscatter Absorption Gas Imaging: New Technique for Gas Visulization. Appered Optic, Jul. 1993, p. 4037–4050, v.32, N21, USA.

Primary Examiner—Constantine Hannaher
Assistant Examiner—Albert Gagliardi
Attorney, Agent, or Firm—David R. Stacey; Larry I. Golden; Larry T. Shrout

[57] ABSTRACT

A method and apparatus for remote detection of gas leak and determination of the relative concentration of a gas using nondispersive infrared absorption of backscattered laser light with background compensation. The method includes source of coherent infrared radiation, sealed reference cell, filled with air with admixture of reference gas of known concentration, sealed control cell filled with air, sensitive elements which are sensitive to radiant fluxes in a determined band of wavelengths. The method includes measuring output signals, calculating the difference of the signals from control cell for different points, the difference of signals from reference cell and control cell, the ratio of said differences and relative concentration, and means for converting said concentration into visual image and audio signal. The apparatus includes camera or video camera to record a visual image of an object at the point where the maximum relative concentration was recorded and laser pointer to indicate a position of invisible infrared beam on a target.

10 Claims, 4 Drawing Sheets

LEAK DETECTION SYSTEM

FIELD OF THE INVENTION

This invention relates to the field of gas sensing devices. More particularly, the present invention relates to a method and apparatus for remote detection of gas leak and determination of the relative concentration of a gas using nondispersive infrared absorption of backscattered laser light with background compensation.

BACKGROUND OF THE INVENTION

The nondispersive infrared (NDIR) technique is widely used for the detection of gas leaks. Such gas analyzers utilize the principle that various gases absorb infrared radiation at characteristic wavelengths. Typically, a narrow band infrared transmission filter is used to isolate the infrared band of interest in NDIR gas analyzers. The NDIR technique advantages include gas detection specificity, measurement stability, and high speed of response. Remote monitoring of gaseous products with no external source of infrared radiation may be realized using specific measurements of infrared radiation and rationalizing the signals from gas-reference cell pairs. Sensitivity of these methods is considerably lower than that of the methods that include infrared laser illuminating and "pumping" up gas plume radiation. Also a presence of moving mechanical parts decreases a reliability and precision of this systems. Another technique of gas leak location comprises directing a beam of coherent high intensity infrared radiation into potential plume direction, and the wave length of the beam is selected such that it energized selected molecules. The imager receives both backscattered laser light and background radiation. When a detectable gas is present, the backscattered laser light is highly attenuated, producing a region of contrast or shadow on the image. This techniques uses an infrared video camera and other technical means, which require a separate source of cooling, which increases the cost of device and maintenance, and reduces the portability of the system. The technique does not eliminate background effects from the signal. These methods and apparatus do not provide a quantitative information about gas concentration in the cloud surrounding leak area. An effectiveness of these methods highly depends on the background properties. Gas visualization apparatus cannot clearly distinguish between the infrared gas absorption information of gas leakage and the background information, are not portable and do not provide a quantitative information of gas concentration. From the other hand, methods using gasfilter correlation technique usually are passive methods with lower sensitivity and precision in case of small leaks at the distance.

It is therefore desirable to provide portable and sensitive means to detect gas leaks at the distance, which will not depend on background properties.

SUMMARY OF THE INVENTION

An object of the present invention, therefore, is to provide a gas leak detection method and apparatus, which requires only a simple portable construction without moving parts, which remotely determines the relative concentration of gas or vapor, and locates the leak site by visual and audio signal at a large distance in working conditions. The present invention will provide remote gas leak control independent of the background and/or surrounding conditions.

I have developed a method and apparatus for generating a visible and audio signal, intensity of which corresponds to the concentration of the gas of interest at the leakage site, with background compensation. The method is based on the registration of the backscattered infrared radiation of the infrared laser. The wavelength of the laser is selected to correspond to the strong absorption band of the gas to be detected. The laser operator scans a laser beam along the areas of the most possible leak locations (flanges, soldered or welded joints, etc.) of the working gas-filled equipment or pipe. The infrared detecting device for detection of the backscattered infrared light, which has been attenuated by the absorbing gas cloud consists of: a pair of cells, including a control cell containing air; and a reference cell containing air and a known percentage of the gas of which the leak is being detected; with the cells in all other respects being identical. A pair of identical infrared detectors are mounted, one behind each cell to register intensity of the infrared radiation in a predetermined wavelength range including the most intense absorption line of the gas of interest. Backscattered infrared light simultaneously passes through both cells and reaches the detectors. Detection occurs by measuring the received infrared radiation in a gas absorption band by both detectors. The electronic device processes the signals of the two said detectors, compares the signals, and calculates their differences and ratios. An output device includes both (i) a visual analog display that shows a dial or bar reading that varies directly, but not necessarily linearly, in relation to the relative concentration of the gas at the leakage site and (ii) an audio alarm indicator that sounds when a leak concentration threshold is detected. According to the relative concentration scale on the screen, the visual analog signal varies when an operator aims a laser beam in close proximity to a leak location and reaches a maximum value at the precise position of the leak. A miniature laser pointer is mounted on a device to indicate the position of an invisible infrared beam on a target.

BRIEF DESCRIPTION OF THE DRAWINGS

The accompanying drawings illustrate the invention. In such drawings.

Figure 1:
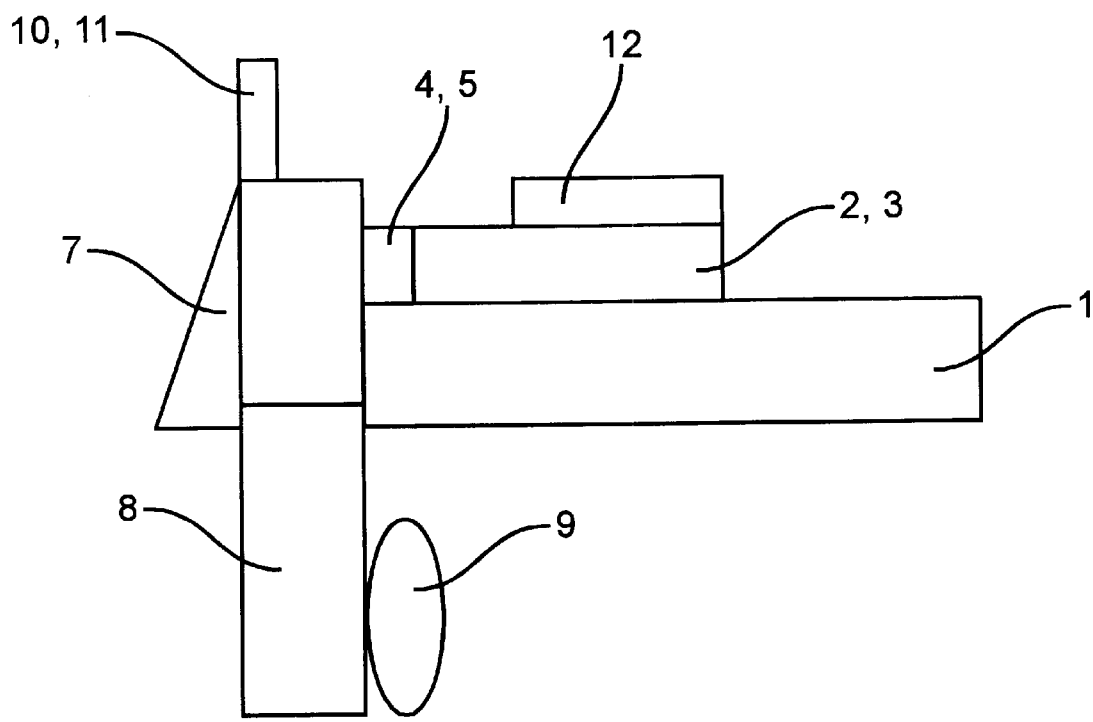
FIG. 1 is a highly diagrammatic representation of a side view of the present invention.

Before one embodiment of the invention is explained in detail, it is to be understood that the invention is not limited in its application to the details of construction and description or illustrated in the drawings. The invention is capable of other embodiments and of being practiced or being carried out in various other ways. Also, it is to be understood that the phraseology and terminology used herein is for purpose of description and should not be regarded as limiting.

DETAILED DESCRIPTION OF THE CONCEPT AND THE PREFERRED EMBODIMENT

Figure 2:
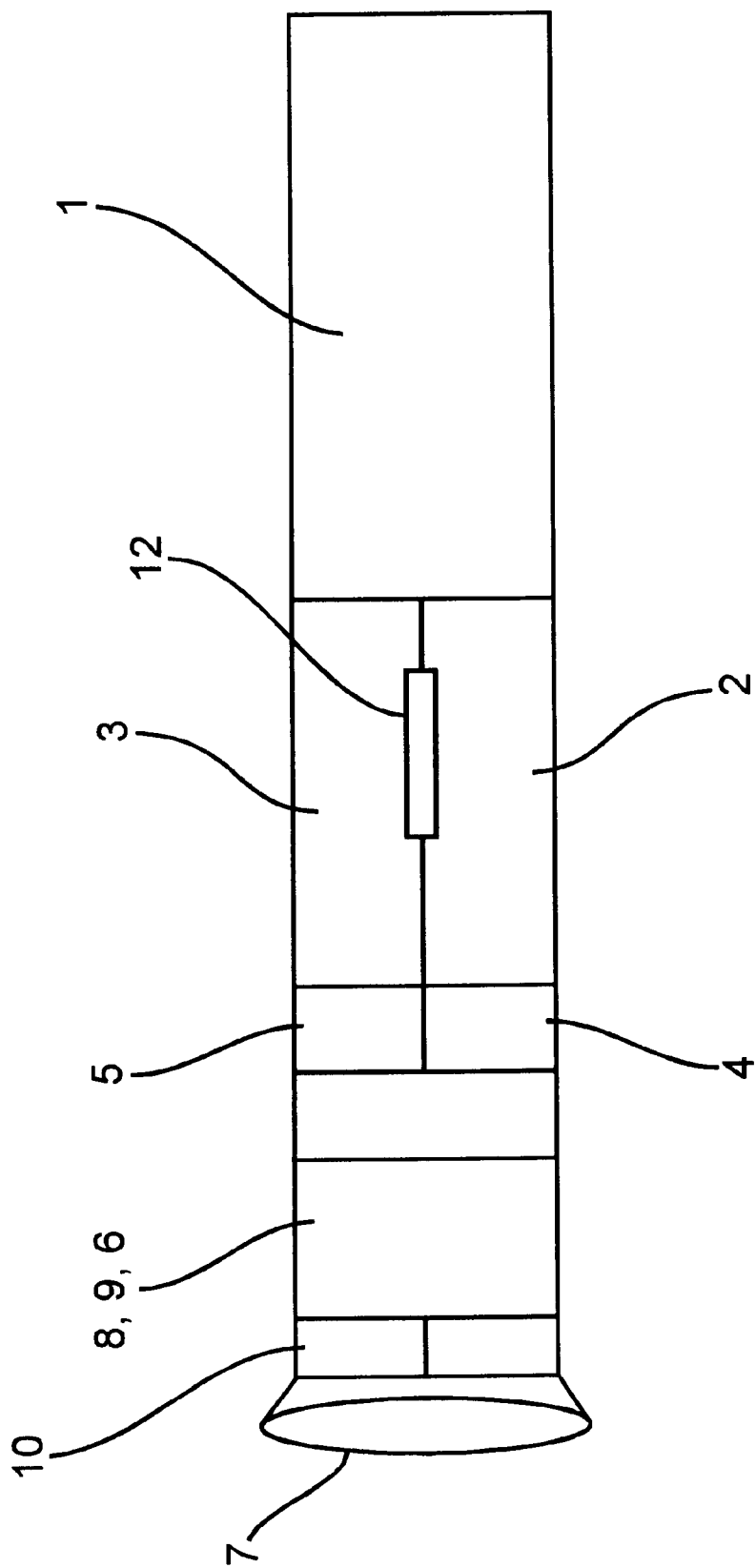
FIG. 2 is a highly diagrammatic representation of a top view of the leak detection system embodying the novel features of the invention.

Details of the leak detection system according to the present invention will be described with reference to FIGS. 1 and 2. The leak detection system includes an infrared laser 1 acting as an infrared emitting device with the laser power supply, two identical gas cells, one of them 2 filled with air (control cell), and another one 3 filled with the mixture of air and gas to be detected with a known concentration (reference cell). Behind each gas cell an infrared sensor or detector (4, 5) is mounted. These IR sensors measure an intensity of infrared beams radiated or reflected from the background and travelling though the gas leak territory. Within this construction, the information detected by the IR detectors is processed in the electronic device 6. The gas leak detection system further includes a visual analog display 7 for displaying the processed information relating to the gas relative concentration at leakage point. All measured and calculated information and all additional information related to the physical constants of gases of interest and data used for calculations are stored in a memory block 8. Operational unit 9 sends commands to audio unit 10 and camera 11 and controls calculations in the electronic device 6. To indicate a position of an invisible infrared beam on a target, an optical laser pointer 12 is mounted on the device.

With this construction, all parts of the leak detection system mentioned above are mounted in one portable unit. The information detected by the infrared detectors is processed and displayed on the screen for observation by the operator. The leak detection system according to the present invention is operable in an active mode when the infrared laser 1 and infrared detectors 4 and 5 are operated, and the resulting detection information is processed and displayed on the screen as the information relating to gas leakage.

The concept of the present invention of background compensation in gas concentration measurement may be understood best by referring to the analysis of the signals measured by both detectors. Let $I_0$ be an intensity of infrared radiation emitted by laser 1, then $I_{BB}$ is an intensity of the backscattered infrared beam that reaches the front windows of the gas cells 2, 3 in the absence of the leak. $I_{BB}$ depends on the backscattering properties of the background, as well as the emission and absorption properties of gases in an ambient atmosphere, in which infrared radiation travels from a laser to the target and back to measuring device. $I_{BB}$ may be described by the equation (4).

In a situation with no gas leak, the gas concentration to be measured equals zero. Let $I_c$ be equal to the portion of backscattered IR radiation, which is absorbed in control cell 2, which contains pure air. Since reference cell 3 is identical to control cell 2 in all other respects except an admixture of the gas to be measured, $I_C$ is also a portion of backscattered radiation absorbed in cell 3. $I_R$ is a portion of IR radiation absorbed in reference cell 3 by a known admixture of the gas of interest. Then detector 4 in the control cell measures $$I_{C0}=I_{BB}-I_C$$

Detector 5 in the reference cell measures $$I_{R0}=I_{BB}-I_C-I_R$$

A differential between two readings simultaneously taken from the outputs of the two detectors, with the device aimed at a region where there is no leak, is equal:

$$I_{C0}-I_{R0}=I_{BB}-I_C-I_{BB}+I_C+I_R=I_R \quad (1)$$

This calculated difference characterizes IR absorption of gas of interest at a known concentration.

In a situation with a gas leak, a certain leakage produces detectable amount of gas of interest with an unknown concentration. A gas cloud attenuates laser radiation for the value $I_L$ due to scattering and absorption of infrared radiation in a close vicinity of a leakage. The first control detector 4 measures $$I_{CL}=I_{BB}-I_C-I_L$$

and reference cell detector 5 measures $$I_{RL}=I_{BB}-I_C-I_R-I_L$$

Then a calculated difference of two signals, simultaneously measured in the control and reference cells, is equal:

$$I_{CL}-I_{RL}=I_R \quad (2),$$

meaning that differential signal depends neither on background and ambient atmosphere properties nor on leak presence. This differential signal should not change for two consequent readings for two regions, whether there is gas leak or not. It is considered dependent only on the content of the cells, which does not change. If the difference has changed, it provides a basis for correcting the new readings and eliminating variations due to changes in background or other atmospheric effects affecting the intensity of backscattered light $I_{BB}$ entering the cells. After proper correction of the differential signal prior to a leak detection procedure, $I_{BB}$ is considered unchanging in the following calculations.

For a particular procedure of leak detection the calculated differential value $I_R$ is a parameter corresponding to the known concentration of the gas (g) admixture in the reference cell $C(g)_R$ and may be determined using the formula:

$$I_R=I_{BB}\exp(-\mu g \cdot l \cdot C(g)_R) \quad (3),$$

where $\mu g$ is a linear absorption coefficient of the gas of interest at a given wavelength, l is an internal length of the cell(s); $I_{BB}$ is backscattered beam intensity.

The value $A(g)=\exp[-\mu g\, l\cdot C(g)_R]$ is constant for a given gas (g), concentration, and length of the cell. $A(g)$ is calculated and stored in memory block 8.

The value of $I_R$, the calculated difference between two simultaneous readings from the outputs of the two detectors behind the control and reference cells, either in the absence of the leak or at any other point, and stored value $A(g)$ may be used for calculation of $I_{BB}$ using the formula:

$$I_{BB}=I_R/A(g), \quad (4)$$

On the other hand, the measured signal must change while the laser beam travels from the point with no leak ($I_{C0}$) to the point in close vicinity of leakage ($I_{CL}$). Some amount of gas of interest is present there, and a signal change, taken from the output of the detector behind the control cell equals:

$$I_{C0}-I_{CL}=I_{BB}-I_C-I_{BB}+I_C+I_L=I_L \quad (5),$$

where $I_L$ is the calculated difference between the current reading $I_{CL}$ and the previously stored reading $I_{C0}$, and it is a portion of laser radiation, which was scattered and absorbed in a gas cloud in a close vicinity of the leakage.

Laser radiation attenuation is due to scattering and absorption of infrared light in a gas cloud. However, if laser 1 emits a narrow wavelength band including the strongest absorption band of the gas of interest, the absorption process will be substantially prevalent to all other attenuating processes, including scattering. Then $I_L$, an attenuated laser radiation, may be estimated by the formula:

$$I_L=I_0\exp[-\mu g \cdot L \cdot C(g)_L] \quad (6),$$

where L is the length of the way, which the laser beam travels through a gas cloud; $C(g)_L$ is an average concentration of gas in the cloud; $\mu g$ is the linear absorption coefficient of the given gas. $I_0$ is an intensity of the incident laser beam, which is then attenuated, when it travels though a gas cloud, then scatters back from a background, and travels back through a cloud again. This intensity may be approximately expressed through $I_L$ and $I_{BB}$ by the simple expression:

$$I_0 = I_L + I_{BB} \quad (7)$$

A system of three equations (4), (6), and (7) contains three variables $I_0$, $I_{BB}$ and $X_g$, where $X_g$ is a product of two variables, L and $C(g)_L$. Solution of this system with respect to the variable $X_g$ gives a formula for the determination of the relative concentration of the gas to be detected in a cloud:

$$X_g = 1/\mu g \cdot \ln[A(g) \cdot I_L/I_R + 1] \quad (8),$$

where parameters $\mu g$ and $A(g)$ are known and stored in memory block 8, and $I_L/I_R$ is a ratio of two differential signals $I_L$ and $I_R$. The difference $I_R$ may be calculated according to the formula (1) prior to the particular leak detection procedure or according to formula (2) at any point and stored in memory block. $I_L$ is calculated according to the formula (5) from the signals measured continuously by two detectors during the leak detection procedure.

Electronic device 6 continuously calculates $X_g$ (8) for given gas from point to point, while a laser beam scans an area of possible leakage, and compares this value with the product of the concentration of the given gas in reference cell $C(g)_R$ and the internal length of the reference cell l. The value of the ratio $X_g/lC(g)_R$ (9) corresponds to the relative concentration of the gas cloud in the vicinity of the leak.

According to the concept of the present invention of background compensation in the gas concentration measurement described above, the method and apparatus for detecting the presence of a gas leak include the steps of:

1) irradiating an area of a possible leak with infrared laser radiation of narrow bandwidth, aiming the device from point to point across the area;
2) at each point at which the device is aimed, measuring infrared radiation in the narrow bandwidth that passes from the point through each of two cells of identical configuration, including a control cell containing air and a reference cell containing air plus gas for which a leak is to be detected;
3) calculating the difference between simultaneous measurements from each cell in response to light from a single point ($I_R$);
4) calculating the difference between sequential measurements from the control cell taken with the device aimed at two different points ($I_L$);
5) calculating the ratio of (a) measured light through the control cell from the two different points to (b) the calculated difference between measurements from each cell ($I_L/I_R$); and
6) generating an output, when the result of the calculation according to the formulas (8) and (9) changes from zero at the point, where there is no leak, to a number characterizing a relative concentration of the gas to be detected at the point of the leakage.

Figure 3:
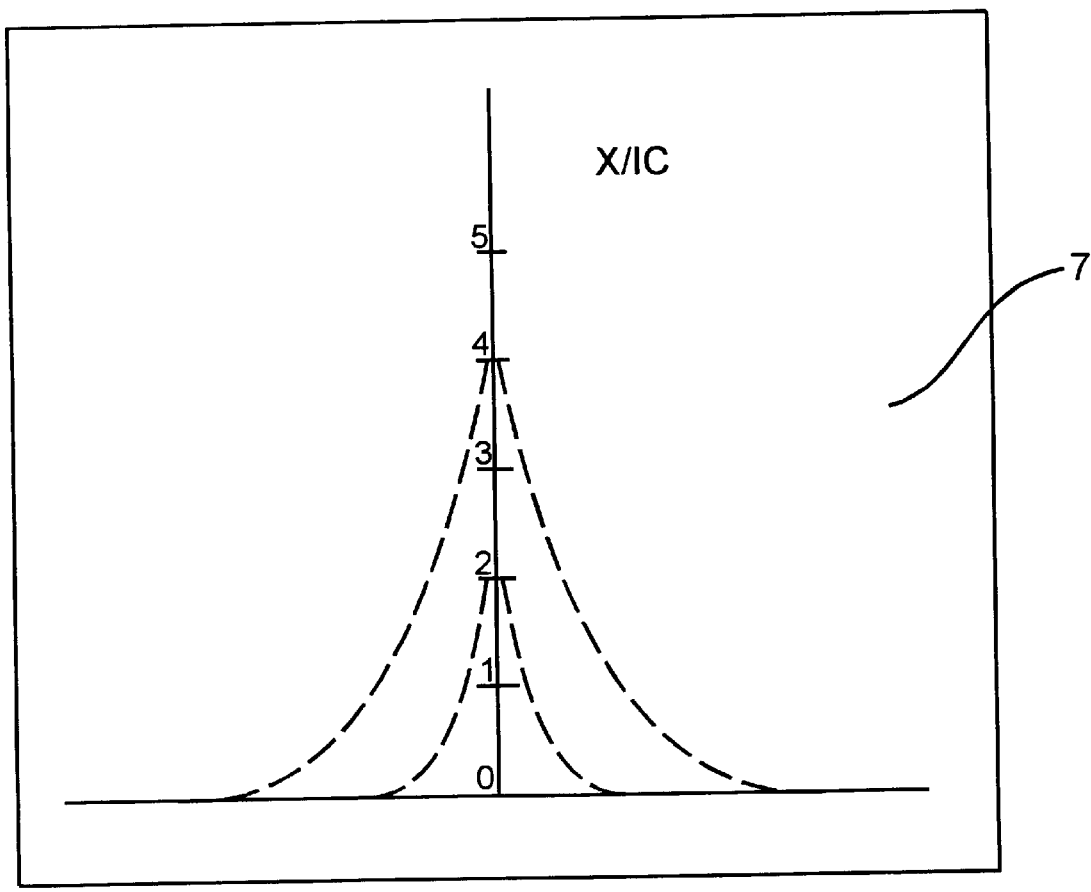
FIG. 3 is a diagrammatic graph showing the appearance of the relative gas concentration in leak vicinity.

Thus, ratio value $X_g/lC(g)_R$ may vary from 0 (no leak) to N, and N=1 when $X_g=lC(g)_R$. Ratio value is converted into a visual signal displayed on the screen 7 located behind the cells with the scale of a relative concentration $X/lC(g)_R$ on the y-axis (FIG. 3).

Electronic device 6 also has technical means to convert the electrical signal into an audio signal, which is sent by operational unit 9 to an audio block 10, warning an operator about approaching the leak location when ratio value exceeds a predetermined level.

When the operator reaches the point with maximum ratio that corresponds to precise leakage location, he sends a signal to a miniature camera 11 or video camera mounted on the top of the measuring device to take a picture of the said location with the pointer in the center of the picture. To indicate a position of an invisible infrared beam on a target, an optical laser pointer 12 is mounted on the device. Information about all maximum value ratios and pictures taken at these points are stored in memory block 8, and may be easily reviewed by comparison of the number of the picture and the relative concentration measured at this point.

The range of the gases that can be measured by using this invention is not limited. Moreover, alternative reference gases and corresponding infrared light sources of selected wavelengths as well as various detectors may be used. By using a tunable IR laser, range of wavelength may be adjusted to include the strongest IR absorption band for virtually any of the gases to be detected in electrical or natural gas industry, as well as for the purposes of environmental control.

For practical purposes gas lasers may be used. Gas lasers are reasonably compact and rugged, and can operate in continuous wave (CW) mode. They have the necessary wavelength stability, output power, and beam divergence.

In an exemplary embodiment of the invention disclosed herein, a continuous wave (CW) line-tunable $CO_2$ laser is used. A $CO_2$ laser is well suited for detection of $NH_3$ (ammonia), $N_2H_4$ (hydrazine), NO (nitrous oxide), $CH_3N_2H_2$ (monomethyl hydrazine), $SF_6$ (sulfur hexafluoride) and many other gases. An infrared He-Ne laser operating at 3.39 $\mu m$ is especially well suited for detection of $CH_4$ (methane) and $C_2H_4$ (ethane).

Figure 4:
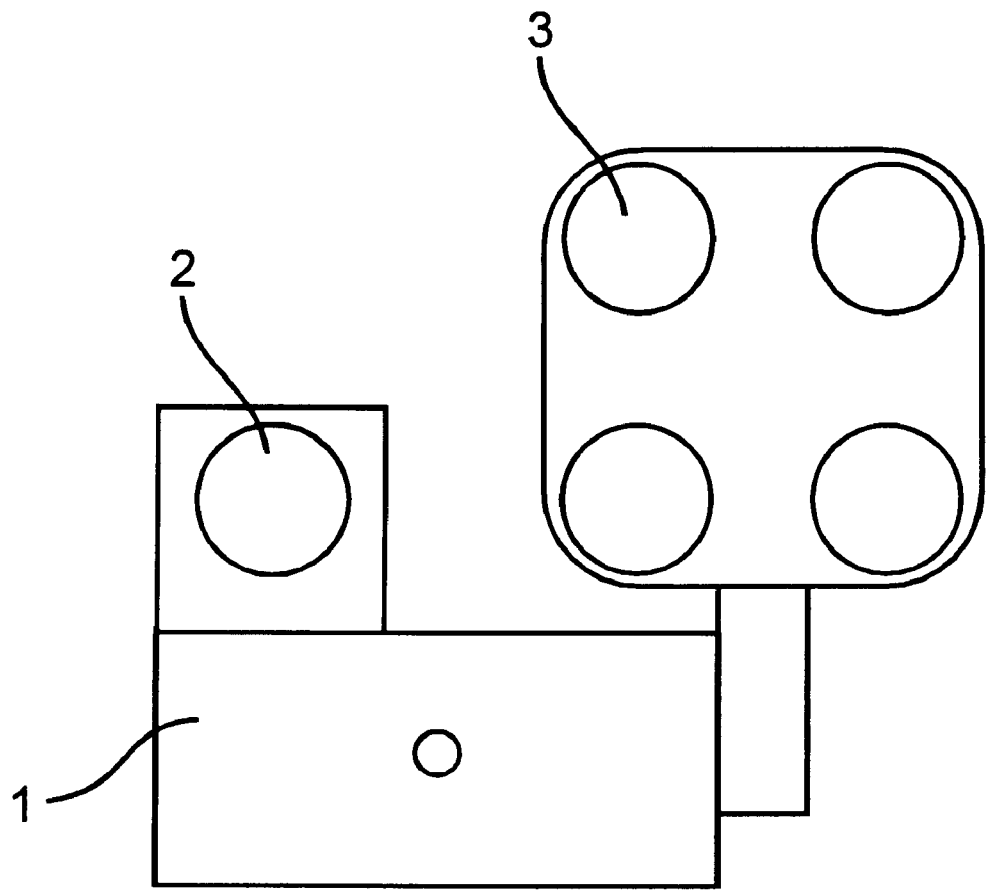
FIG. 4 is a diagrammatic representation of a revolving block of reference cells suitable for use in detecting different gases.

The device may include a revolving set (FIG. 4) of reference cells, each of them containing a different gas of interest of given concentration, and which are identical in all other respects.

Another version of the device includes a kit, which contains a said set of reference cells, which may be inserted into a single cell holder.

The laser wavelength adjustment, as well as data entry of the particular gas parameters, such as $\mu g$, $A(g)$, and $lC(g)_R$ for calculations must follow every change of the reference cell.

I claim:

1. Method for detecting the presence of a gas leakage, comprising:

irradiating the area of a possible leak with infrared laser radiation at a single wavelength, which is absorbed by the gas and backscattered or reflected from the irradiated area;

detecting backscattered laser radiation from the irradiated area;

continuous processing of the detected signals from two cells of identical configuration;

continuous calculation of differential signals, their ratios, and relative concentrations;

producing a visual image and audio signal related to the said relative concentrations when the gas is present in said irradiated area.

2. Method of claim 1 wherein the step of irradiating an area is performed by scanning an area with laser unmodulated radiation.

3. Method of claim 1 wherein the method of calculations of a relative concentration of the gas based on radiation measurement is developed to compensate background and ambient atmosphere influence.

4. Method of claim 1 wherein the steps of detecting radiation from the irradiated area are performed by measuring the radiation by two identical infrared detectors.

5. The method in claim 4 wherein the backscattered radiation is measured after it passes through two sealed cells of identical configuration.

6. The method in claim 5 wherein one of the said cells is filled with air, and another one with the mixture of air with the reference gas, which is supposed to be detected.

7. A method of claim 6 wherein to detect other gases present in said irradiated area a revolving set of reference cells, each containing a different reference gas is employed.

8. A method in claim 5 wherein a cell with admixture of one reference gas may be replaced in a reference cell holder with another cell of identical configuration, but containing a different reference gas.

9. A method of claim 1 wherein a miniature camera or video camera records a visual image of the area where a maximum relative concentration of gas was detected.

10. A method of claim 1 wherein an optical laser pointer is used to indicate the position of said irradiated area.

* * * * *